United States Patent [19]

Lang et al.

[11] Patent Number: 4,950,478

[45] Date of Patent: * Aug. 21, 1990

[54] COSMETIC COMPOSITIONS CONTAINING NATURAL ESSENCES AND BENZYLIDENECAMPHOR DERIVATIVES

[75] Inventors: Gerard Lang, Saint Gratien; Andre Deflandre, Orry-la-Ville; Irena Beck, Villepinte, all of France

[73] Assignee: L'Oreal, Paris, France

[*] Notice: The portion of the term of this patent subsequent to Mar. 15, 2005 has been disclaimed.

[21] Appl. No.: 573,143

[22] Filed: Jan. 23, 1984

[30] Foreign Application Priority Data

Jan. 26, 1983 [LU] Luxembourg .................... 84608

[51] Int. Cl.$^5$ ................... A61K 7/06; A61K 7/42; A61K 7/48; A61K 9/12
[52] U.S. Cl. ................... 424/47; 424/DIG. 5; 424/59; 424/60; 424/65; 424/70; 424/73
[58] Field of Search ................... 424/73, 47, 59, 60, 424/45

[56] References Cited

U.S. PATENT DOCUMENTS

| | | | |
|---|---|---|---|
| 4,061,730 | 12/1977 | Kalopissis et al. | 424/59 |
| 4,240,450 | 12/1980 | Grollier et al. | 424/70 |
| 4,290,974 | 9/1981 | Bouillon et al. | |
| 4,323,549 | 4/1982 | Bouillon et al. | 424/45 |
| 4,406,880 | 9/1983 | Bouillon et al. | |
| 4,421,739 | 12/1983 | Bouillon et al. | 424/47 |
| 4,445,521 | 5/1984 | Grollier et al. | 132/7 |
| 4,585,597 | 4/1986 | Lang et al. | |
| 4,588,839 | 5/1986 | Lang et al. | |
| 4,654,434 | 3/1987 | Lang et al. | |
| 4,663,088 | 5/1987 | Lang et al. | |
| 4,731,200 | 3/1988 | Lang et al. | |

FOREIGN PATENT DOCUMENTS

| | | | |
|---|---|---|---|
| 1492322 | 1/1970 | Fed. Rep. of Germany | 424/59 |
| 1024465 | 1/1953 | France | 424/59 |
| 2004142 | 3/1969 | France | 424/332 |
| 2199971 | 4/1974 | France | 424/59 |
| 2236515 | 2/1975 | France | 424/59 |
| 2237882 | 2/1975 | France | 424/59 |
| 2282426 | 3/1976 | France | 424/59 |
| 2309523 | 11/1976 | France | 424/59 |
| 2360301 | 3/1978 | France | 424/59 |
| 2383904 | 10/1978 | France | 424/59 |
| 2402647 | 4/1979 | France | 424/59 |
| 2409751 | 6/1979 | France | 424/59 |
| 2421878 | 11/1979 | France | 424/59 |
| 2430938 | 2/1980 | France | 424/59 |
| 1310810 | 3/1973 | United Kingdom | 424/59 |
| 1367539 | 9/1974 | United Kingdom | 424/60 |
| 1573370 | 8/1980 | United Kingdom | 424/59 |

OTHER PUBLICATIONS

Markland, Cosmetics & Toiletries, 3/1976, vol. 91, pp. 79 to 81.
Pathak et al., Journal of Investigative Dermatology, vol. 32, 1959, pp. 509 to 518 & 255 to 262.
Bennett, The Cosmetic Formulary, 1937, pp. 83 and 84.
Finnemore, 7/1932, Essential Oils, pp. 413 to 431.
Fitzpatrick et al., Journal of Investigative Dermatology, 1958, vol. 32, pp. 229 to 231.
Girard et al., "intéret en Cosmétique d'une Essence de Bergamote Non Phototoxique", 1981, 39–44.
Harry, "Modern Cosmeticology", 1962, pp. 73–92; 219–220; pp. 502–504.
Chem. Abstr. 156354r, vol. 95(9):364 (Nov., 1981).
Marzulli et al., "Perfume Phototoxicity", J. Soc. Cosmet. Chem. 21: 695-715 (Sep. 17, 1970).
Morliere et al., Photochem. Photobiol. 36:395-399 (1982).
Chem. Abstr. 66414v, vol. 86:117 (1977).

*Primary Examiner*—Dale R. Ore
*Attorney, Agent, or Firm*—Fleit, Jacobson, Cohn, Price, Holman & Stern

[57] ABSTRACT

The present invention relates to a cosmetic composition comprising a natural essence containing a phototoxic dose of furocoumarin, and 0.01 to 2% by weight of at least one benzylidenecamphor derivative filtering out UV-A radiation and chosen from among 3-p-oxybenzylidenebornan-2-ones, 3,3'-terephthalylidenedicamphors optionally sulfonated in the 10-position of the camphor, p-(3-methylidenecamphor)-cinnamic acid derivatives, 3,3'-terephthalylidenedicampho-10-sulfonamides or 3,3'-terephthalylidenedicampho-10,10'-disulfonamides.

It is also possible to incorporate into the composition a UV-B filter chosen from among: benzylidenecamphor, p-methylbenzylidenecamphor, benzylidenecamphor derivatives containing a quaternary ammonium radical on the benzene nucleus in the para position relative to the bornylidene radical, benzylidenecamphor derivatives sulphonated on the methyl radical in the 10-position of the camphor or in the 3'-position of 4'-position on the benzene nucleus, p-methylbenzylidene-camphor derivatives substituted on the p-methyl group, or other 3-benzylidenecamphor derivatives filtering out UV-B radiation.

The effect of the benzylidenecamphor derivative is to deactivate the furocoumarins excited by UV radiation and to reduce their phototoxicity.

20 Claims, No Drawings

COSMETIC COMPOSITIONS CONTAINING NATURAL ESSENCES AND BENZYLIDENECAMPHOR DERIVATIVES

The present invention relates to cosmetic compositions containing natural essences and benzylidenecamphor derivatives.

It has been known for a very long time that natural essences such as bergamot oil and lemon oil, contained in various cosmetics, perfumes and toilet water, are involved in certain skin diseases which appear as violent erythemas and eczematoid lesions, followed by non-uniform residual pigmentations. These skin reactions, which require exposure to ultraviolet light, are referred to as "phototoxic reactions". The compounds responsible for this phototoxicity are furocoumarins, the main representative of this family in bergamot oil being bergaptene, or 5-methoxyfurocoumarin, or alternatively 5-methoxypsoralene (5-MOP), of the formula:

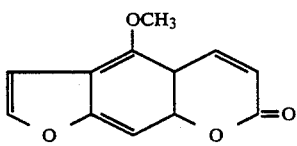

This compound is phototoxic, as are the majority of linear furocoumarins such as, for example, furocoumarin itself and 8-methoxyfurocoumarin. 5-Methoxyfurocoumarin is responsible for skin reactions at a concentration of 10 ppm or above, which explains that, to prevent any risk of skin disease, the use of more than 0.1 to 0.3% of bergamot oil on the skin is generally avoided, this oil containing 3000 to 7500 ppm of 5-methoxyfurocoumarin.

This shows the advantage of removing the furocoumarins from natural essences such as bergamot oil and lemon oil, in order to protect the health of people induced to using cosmetic products perfumed with such essences.

On account of the economic importance of natural essences, detoxification methods have been proposed, in particular for bergamot oil, which is used in cosmetics not only for its olfactory properties but also for its properties of accelerating the pigmentation of the skin, which are described, in particular, in French Patent Applications No. 2,360,301 and No. 2,409,751. These methods employ vacuum distillation of the volatile fraction of the bergamot oils; the distillation residue is then saponified with alcoholic potassium hydroxide in order to convert the furocoumarins to cinnamic acid derivatives by opening of the lactone group, and then extracted with a hydrocarbon after the alcohol has been evaporated off; the extraction solution is neutralised by washing with water, and the residue obtained after the solvent has been evaporated off is incorporated into the volatile fraction.

The bergamot oils treated by this process and containing 40 ppm or less of 5-methoxyfurocoumarin are only very slightly phototoxic, as shown in the publication by J. Girard et al. in "Parfums, cosmetiques, aromes" no. 38, April-May 1981, pages 39–44. However, such methods for the detoxification of natural essences are complicated and expensive and have the disadvantage of considerably modifying the olfactory properties of the essences treated.

Attempts have therefore been made to find another means of detoxifying natural essences by eliminating the toxic effect due to furocoumarins.

It is known that, when furocoumarins absorb ultraviolet light, they are electronically excited. It is the triplet excited level which is the precursor state of all known photobiological reactions.

Now, the Applicant Company has observed that, totally surprisingly, certain benzylidenecamphor derivatives which filter out UV-A radiation are capable of deactivating the triplet level of furocoumarins according to the equation:

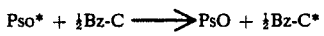

Pso denoting psoralene and Bz—C denoting the benzylidenecamphor derivative.

This results in a molecule of furocoumarin in the unexcited ground state and an excited molecule of benzylidenecamphor derivative, which then deactivates itself without any reaction other than a purely intramolecular E—Z isomerisation:

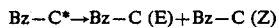

These benzylidene camphor derivatives are as follows:

the 3-p-oxybenzylidenebornan-2-ones of French patent No. 2,430,938, having the formula:

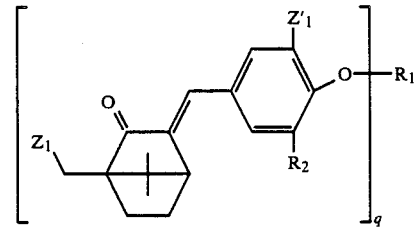

in which:

$Z_1$ and $Z'_1$ respectively denote a hydrogen atom, a radical $SO_3H$ or a salt of this sulphonic acid with an inorganic or organic base, at least one of the two radicals $Z_1$ or $Z'_1$ representing a hydrogen atom;

$R_1$ denotes a hydrogen atom, an optionally branched alkyl radical containing 2 to 18 carbon atoms, an alkenyl radical containing 3 to 18 carbon atoms or a radical

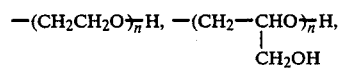

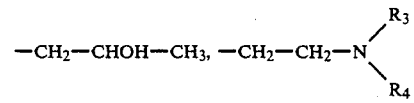

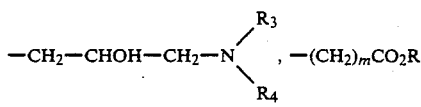

in which R denotes H, an alkyl radical containing 1 to 8 carbon atoms, $-(CH_2)_3-SO_3H$ or a salt of this acid with an organic or inorganic base, or alternatively a divalent radical $-(CH_2)_m$ or $-CH_2-CHOH-CH_2$, m having the values 1 to 10 and n having the values 1 to 6, and $R_3$ and $R_4$ each representing a hydrogen atom or an optionally branched or hydroxylated alkyl radical, or together forming an aminoaliphatic heterocycle with the nitrogen atom;

$R_2$ denotes a hydrogen atom, an alkoxy radical containing 1 to 4 carbon atoms or a divalent radical $-O-$ joined to the radical $R_1$ in the case where the latter is also divalent; and q denotes 1 or 2, it being understood that if q has the value 2, $R_1$ is a divalent radical, and that if $R_1$ denotes hydrogen, $R_2$ also denotes hydrogen; moreover, if $R_2$ denotes alkoxy, $R_1$ can also denote methyl;

the benzylidenecamphors described in Belgian Patent Application No. 211,022, having the formula:

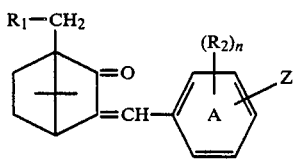

in which:

$R_1$ denotes a hydrogen atom or a radical $-SO_3^\oplus M^\ominus$, in which M denotes a hydrogen atom, an alkali metal or a group

$R_3$ denoting a hydrogen atom or a $C_1$ to $C_4$ alkyl or hydroxyalkyl radical;

n=0, that is to say $R_2$ denotes a hydrogen atom; and Z represents a group

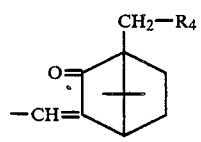

in which $R_4$ has the same meanings as $R_1$ and can be equal to $R_1$ or different from $R_1$, or alternatively a group

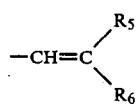

in which $R_5$ denotes a hydrogen atom, a $C_1$ to $C_4$ alkyl radical, an aryl radical optionally substituted by halogen atoms or by $C_1$ to $C_4$ alkyl or alkoxy groups, or a group $-CN$, $-COOR_7$ or

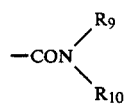

and $R_6$ denotes a group $-COOR_8$ or

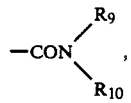

$R_7$ and $R_8$, which are identical or different, being alkyl, alkenyl, cycloalkyl or aralkyl radicals containing at most 20 carbon atoms, which are optionally substituted by hydroxyl, alkoxy, amine or quaternary ammonium groups, and $R_9$ and $R_{10}$, which are identical or different, denoting a hydrogen atom or alkyl, alkenyl, cycloalkyl or aralkyl radicals containing at most 20 carbon atoms, which are optionally substituted by hydroxyl, alkoxy, amine or quaternary ammonium groups, or alternatively if $R_5$ denotes a hydrogen atom or an alkyl or optionally substituted aryl radical, $R_6$ can also represent a radical $-COO^\ominus M^\oplus$, M being defined as above, the two methylidenecamphor radicals, on the one hand, and Z, on the other hand, being attached to the aromatic nucleus A in the para position relative to one another; and the sulphonamides derived from benzylidene-camphor described in Belgian Patent Application No. 211, 134, having the formula:

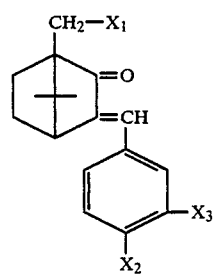

in which:

$X_1$ denotes the radical Y;
$X_2$ denotes a radical Z; and
$X_3$ denotes a hydrogen atom,
Y denoting the group

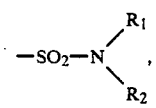

in which $R_1$ denotes a hydrogen atom or a $C_1-C_4$ alkyl or hydroxyalkyl radical and $R_2$ denotes a hydrogen atom, a linear or branched alkyl or alkenyl radical or a cycloalkyl, aryl or aralkyl radical, it being possible for these various $C_1-C_{20}$ radicals to be substituted by one or more hydroxyl, alkoxy or dialkylamino groups, it being impossible for $R_1$ and $R_2$ simultaneously to denote a hydrogen atom, and Z denoting one of the following groups:

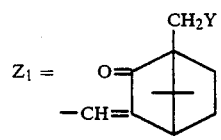

which Y has the abovementioned meaning, or

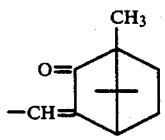

The experiments carried out by the Applicant Company have shown that a concentration of benzylidenecamphor derivative filtering out UV-A radiation, as defined above, of the order of $4.10^{-3}$ mol per liter is sufficient to deactivate 80% of the excited furocoumarin molecules. Under these conditions, the phototoxic activity of a solution containing furocoumarins and $4.10^{-3}$ mol per liter of benzylidenecamphor derivative would be 5 times lower than the phototoxic activity of an identical solution not containing benzylidenecamphor derivative.

The object of the present invention is therefore to reduce the photoxicity of the furocoumarins contained in natural essences by the addition of at least one of the benzylidenecamphor derivatives defined above, which have the property of picking up the electronic excitation energy of the furocoumarins and degrading it in the form of heat energy after isomerisation.

The present invention relates to a cosmetic composition containing a phototoxic dose of furocoumarin and at least one benzylidenecamphor derivative filtering out UV-A radiation and chosen from amongst the above compounds.

A phototoxic dose can be defined as being equal to at least 10 ppm of bergaptene.

Experiments carried out on guinea-pigs have made it possible to demonstrate the considerable reduction in erythema or the absence of erythema on the skin to which the composition has been applied, after the animal has been exposed to UV-A radiation.

The following may be mentioned as benzylidenecamphor derivatives filtering out UV-A radiation which are particularly preferred according to the invention: 3,3'-terephthalylidenedicampho-10,10'-disulphonic acid, 3,3'-terephthalylidenedicampho-10-sulphonic acid, 4-(ethyl 2'-carboxyethylacrylate)-benzylidenecamphor, 4'-butoxy-3'-methoxy-3-benzylidenebornanone and also their salts.

According to a preferred embodiment of the invention, the cosmetic composition containing a phototoxic dose of furocoumarin and at least one benzylidenecamphor derivative filtering out UV-A radiation also contains at least one compound filtering out UV-B radiation which is compatible with the abovementioned UV-A filters.

The compounds filtering out UV-B radiation which are used according to the invention are chosen from amongst:
  benzylidenecamphor;
  p-methylbenzylidenecamphor;
  benzylidenecamphor derivatives containing a quaternary ammonium radical on the benzene nucleus in the para position relative to the bornylidene radical, according to French Patent No. 2,199,971, having the formula:

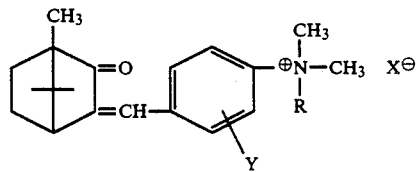

in which:
  R represents a hydrogen atom or an alkyl group containing 1 to 12 carbon atoms,
  Y represents a halogen, a methyl group or a hydrogen atom, and
  $X^{\ominus}$ represents a halide, an arylsulphonate, an alkylsulphonate, a camphosulphonate or an alkylsulphate;
benzylidenecamphor derivatives sulphonated on the methyl radical in the 10-position of the camphor or in the 3'-position or 4'-position on the benzene nucleus, according to French patent Nos. 2,236,515, 2,282, 426, respectively having the formulae:

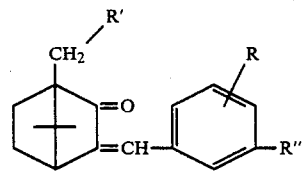

in which R denotes a hydrogen atom, a halogen atom such as Cl or F, or an alkyl radical containing 1 to 4 carbon atoms, and R' and R" each denote a hydrogen atom or a radical —$SO_3M$, in which M denotes H, an organic ammonium group or a metal, at least one of the radicals R' and R" not having the meaning H, and

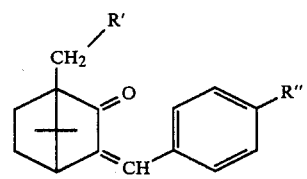

in which R' denotes a hydrogen atom or a radical —$SO_3M$ and R" denotes $SO_3M$, in which M denotes H, an organic ammonium group or a metal;

p-methylbenzylidenecamphor derivatives substituted on the p-methyl group, according to French patent Nos. 2,383,904, 2,402,647, 2,421,878, respectively having the formulae:

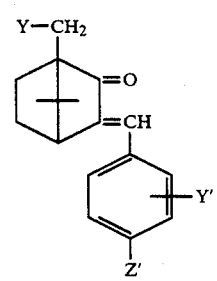

in which Y and Y' denote H or SO$_3$H and the corresponding salts with organic or inorganic bases, at least one of the radicals Y and Y' having the meaning H; and Z' denotes the group —CH$_2$R, —CHR'R', —CHO or 'COOR'', in which R=—OR$_4$, —OCOR$_5$, —SR$_6$, —CN or —COOR'', R$_4$=H, alkyl, polyoxyethylene or substituted or unsubstituted aryl, R$_5$=alkyl, alkenyl, aryl or an aromatic or non-aromatic heterocycle containing 5 to 6 ring members, and R$_6$=H, alkyl, carboxyalkyl, amino-alkyl, hydroxyalkyl, aryl or alanin-3-yl, R'=—OR'$_4$ or —SR'$_6$, in which R'$_4$ and R'$_6$ can respectively have the same meanings as R$_4$ and R$_6$, except for the meaning hydrogen, and R''=hydrogen or alkyl, and

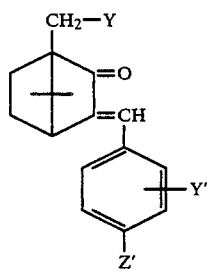

in which Y denotes H or SO$_3$H and the corresponding salts with organic or inorganic bases;

Y' denotes H; and

Z' denotes the group —CH$_2$I, —CH$_2$R, —CHR'R', —CHO or —COOR'', in which R=—OR$_4$, —O-COR$_5$, —SR$_6$, —CN or —COOR'', R$_4$=H, alkyl, polyoxyethylene, substituted or unsubstituted aryl, menthyl or dialkylaminoalkyl, R$_5$=alkyl, alkenyl, aryl or an aromatic or non-aromatic heterocycle containing 5 to 6 ring members, and R$_6$=H, alkyl, carboxyalkyl, aminoalkyl, hydroxyalkyl, aryl or alanin-3-yl, R'=—OR'$_4$ or —SR'$_6$, in which R'$_4$ and R'$_6$ can respectively have the same meanings as R$_4$ and R$_6$, except for the meanings hydrogen, polyoxyethylene, hydroxyalkyl, alanin-3-yl and aryl, and R''=hydrogen or alkyl;

the benzylidenecamphors described in Belgian Patent Application No. 211,002, having the formula:

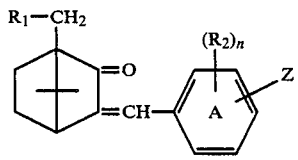

in which:

R$_1$ denotes a hydrogen atom or a radical —SO$_3^\ominus$M$^\oplus$, in which: M denotes a hydrogen atom, an alkali metal or a group $\overset{\oplus}{\text{N}}$(R$_3$)$_4$, R$_3$ denoting a hydrogen atom or a C$_1$ to C$_4$ alkyl or hydroxyalkyl radical; R$_2$ denotes a linear or branched C$_1$ to C$_4$ alkyl radical C$_1$ to C$_4$ alkoxy radical, n being an integer ranging from 0 to 4; if n≧2, the radicals R$_2$ can be identical or different; and Z represents a group

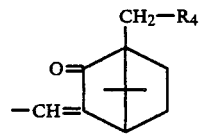

in which R$_4$ has the same meanings as R$_1$ and can be equal to R$_1$ or different from R$_1$, or alternatively a group

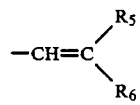

in which: R$_5$ denotes a hydrogen atom, a C$_1$ to C$_4$ alkyl radical, an aryl radical optionally substituted by halogen atoms or by C$_1$ to C$_4$ alkyl or alkoxy groups, or a group —CN, —COOR$_7$ or

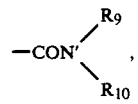

and R$_6$ denotes a group —COOR$_8$ or

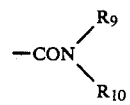

R$_7$ and R$_8$, which are identical or different, being alkyl, alkenyl, cycloalkyl or aralkyl radicals containing at most 20 carbon atoms, which are optionally substituted by hydroxyl, alkoxy, amine or quaternary ammonium groups, and R$_9$ and R$_{10}$, which are identical or different, denoting a hydrogen atom or alkyl, alkenyl, cycloalkyl or aralkyl radicals containing at most 20 carbon atoms, which are optionally substituted by hydroxyl, alkoxy, amine or quaternary ammonium groups, or alternatively if R$_5$ denotes a hydrogen atom or an alkyl or optionally substituted aryl radical, R$_6$ can also represent a radical —COO$^\ominus$M$^\oplus$, M being defined as above, the two methylidenecamphor radicals, on the one hand, and Z, on the other hand, being attached to the aromatic nucleus A in the meta position relative to one another; they can be attached in the para position if n≠0; and the sulphonamides derived from benzylidene-camphor described in Belgian Patent Application No. 211,134, having the formula:

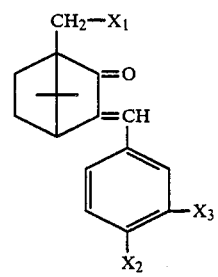

in which X$_1$ denotes a hydrogen atom or the radical Y;

$X_2$ denotes a hydrogen or halogen atom, a $C_1$-$C_4$ alkyl or alkoxy radical or a radical Y or Z; and $X_3$ denotes a hydrogen or halogen atom, a $C_1$-$C_4$ alkyl or alkoxy radical or a radical Y or Z, or alternatively $X_2$ and $X_3$ together form an alkylenedioxy group in which the alkylene group contains 1 or 2 carbon atoms, Y denoting the group

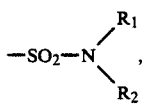

in which $R_1$ denotes a hydrogen atom or a $C_1$-$C_4$ alkyl or hydroxyalkyl radical and $R_2$ denotes a hydrogen atom, a linear or branched alkyl or alkenyl radical or a cycloalkyl, aryl or aralkyl radical, it being possible for these various $C_1$-$C_{20}$ radicals to be substituted by one or more hydroxyl, alkoxy or dialkylamino groups, it being impossible for $R_1$ and $R_2$ simultaneously to denote a hydrogen atom, and Z denoting one of the following groups:

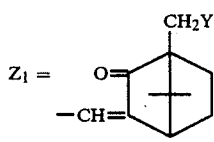

in which: Y has the abovementioned meaning, or

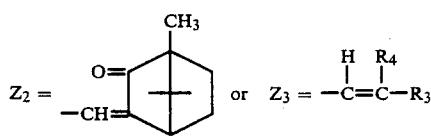

in which $R_3$ denotes a hydrogen atom or a group —CN or —$COR_5$ and $R_4$ denotes a group —$COR_6$, $R_5$ and $R_6$, which are identical or different, being $C_1$-$C_{20}$ alkoxy or alkylamino groups, with the proviso that one of the symbols $X_1$, $X_2$ and $X_3$ is different from the other two and that (a) when $X_1$ denotes a hydrogen atom, $X_2$ and $X_3$ are different from one another and cannot take the meanings $Z_2$ and $Z_3$, one of the two necessarily having the meaning Y or $Z_1$, and (b) when $X_1$ has the meaning Y, $X_2$ and $X_3$ are different from Y and cannot simultaneously take the meaning $Z_1$, $Z_2$ or $Z_3$, and, moreover, if $X_2=Z_1$ or $Z_2$, $X_3$ does not denote a hydrogen atom.

The following may be mentioned as particularly preferred compounds filtering out UV-B radiation which are used according to the invention: 4-[(2-oxo-3-bornylidene)-methyl]-phenyltrimethylammonium methylsulphate, p-methylbenzylidenecamphor, N-(2-ethylhexyl)-benzylidene-campho-10-sulphonamide, 3-(2-oxo-3-bornylidenemethyl)-benzenesulphonic acid, 2-methyl-5-(2-oxo-bornylidenemethyl)-benzenesulphonic acid, 3-benzylidene-2-oxobornane-10-sulphonic acid and also their salts.

The cosmetic composition according to the invention generally contains 0.01 to 2% and preferably 0.1 to 1% by weight of benzylidenecamphor derivative(s), relative to the total weight of the composition. It contains natural essences such as bergamot oil and lemon oil.

The cosmetic composition according to the invention can be presented in the widest variety of forms normally used in cosmetics, and especially in the form of a solution, a lotion, an emulsion such as a cream or a milk, or a gel, or can be packaged in an aerosol can or as a solid stick.

It can contain the customary cosmetic adjuvants such as thickeners, softeners, humectants, superfatting agents, emollients, wetting agents, surface-active agents, preservatives, anti-foam agents, oils, waxes, serving to colour the comdyestuffs and/or pigments position itself or the skin, or any other ingredient normally used in cosmetics.

As the solvent for solubilising the benzylidenecamphor derivative, it is possible to use an oil, a wax, a monoalcohol, a polyol or a mixture of these. The particularly preferred monoalcohols or polyols are ethanol, isopropanol, propylene glycol or glycerol.

One embodiment of the invention is an emulsion in the form of a cream or milk comprising, in addition to the abovementioned benzylidenecamphor derivative and a natural essence constituting the perfume, fatty alcohols, ethoxylated fatty alcohols, fatty acid esters or fatty acid triglycerides, fatty acids, lanoline, natural and synthetic oils, and waxes, in the presence of water.

Another embodiment consists of lotions such as oily-alcoholic lotions based on lower alcohols such as ethanol, or on glycols such as propylene glycol, and/or on polyols such as glycerol, and on fatty acid esters or fatty acid triglycerides.

The cosmetic composition of the invention can also be an oily-alcoholic gel comprising one or more lower alcohols such as ethanol, propylene glycol or glycerol, and a thickener such as silica, in the presence of oil.

The cosmetic composition according to the invention can also be presented in the form of a shaving cream or foam. It then generally contains soaps to which fatty acids and softeners such as glycerol have been added if appropriate. If it is presented in the form of a foam, it can contain foam stabilisers and is packaged in an aerosol device in the presence of propellant gases, according to well-known techniques.

The invention will be illustrated more clearly by the non-limiting examples which follow.

EXAMPLE 1

Perfumed Mositurising Cream

| PERFUMED MOISTURISING CREAM | |
|---|---|
| Natural essence containing 30% of bergamot oil | 1.6 g |
| Triethanolamine salt of 3,3'-terephthalylidene-dicampho-10,10'-disulphonic acid | 0.5 g |
| Cetyl-stearyl alcohol + oley-cetyl alcohol oxyethyleneated with 25 mol of ethylene oxide | 7 g |
| | 2 g |
| Glycerol monostearate | 2 g |
| Vaseline oil | 15 g |
| Dimethylpolysiloxane | 1.5 g |
| Cetyl alcohol | 1.5 g |
| Glycerol | 20 g |
| Preservatives | 0.3 g |
| Distilled water q.s. | 100 g |

This emulsion is prepared by the conventional techniques. The fatty phase is poured, with vigorous agitation, into the aqueous phase containing the water-soluble components, heated to 85°. After vigorous agitation for 10 minutes, the mixture is left to cool with moderate agitation; at about 40° C., the natural essence is added and the emulsion is allowed to return to ambient temperature.

This cream contains 17 ppm of 5-methoxypsoralene.

EXAMPLE 2

Perfumed Body Milk

| PERFUMED BODY MILK | |
|---|---|
| Natural essence containing 50% of bergamot oil | 1.2 g |
| 4-[(2-Oxo-3-bornylidene)-methyl]-phenyltrimethylammonium methyl-sulphate | 0.3 g |
| 4'-Butoxy-3'-methoxy-3-benzylidenebornanone | 0.2 g |
| Cetyl-stearyl alcohol + oleyl-cetyl alcohol oxyethyleneated with 25 mol of ethylene oxide | 5 g |
| Vaseline oil | 6 g |
| Isopropyl myristate | 3 g |
| Silicone oil | 1 g |
| Cetyl alcohol | 1 g |
| Preservatives | 0.2 g |
| Sterile demineralised water q.s. | 100 g |

The emulsion is prepared in a manner similar to that described in Example 1; in this case, the 4-[(2-oxo-3-bornylidene)-methyl]-phenyltrimethylammonium methyl-sulphate is dissolved in the aqueous phase.

The 4-[(2-oxo-3-bornylizene)-methyl]phenyltrimethylammoniun methyl-sulphate can be replaced by 0.3 g of the diethanolamine salt of 3 (2-oxo-3-bornylidenemethyl)-benzenesulphonic acid.

This milk contains 20.4 ppm of 5-methoxypsoralene.

EXAMPLE 3

| PERFUMED BODY OIL | |
|---|---|
| Natural essence containing 5% of bergamot oil | 8 g |
| Triethanolamine salt of 3,3'-terephthalylidene-dicampho-10,10'-disulphonic acid | 0.3 g |
| N-(2-Ethylhexyl)-3-benzylidenecampho-10-sulphonamide | 0.3 g |
| 96° strength ethanol | 43.5 g |
| Triglycerides of $C_8$-$C_{12}$ fatty acids q.s. | 100 g |

This oil contains 14 ppm of 5-methoxypsoralene.

EXAMPLE 4

Shaving Cream

| SHAVING CREAM | |
|---|---|
| Natural essence containing 50% of bergamot oil | 1.5 g |
| Triethanolamine salt of 3,3'-terephthalylidene-dicampho-10-sulphonic acid | 0.4 g |
| p-Methylbenzylidenecamphor | 0.2 g |
| Stearic acid | 25 g |
| Coconut oil | 8 g |
| Olive oil | 2 g |
| Cetyl alcohol | 1 g |
| Sorbitol | 3.5 g |
| 42° Be strength potassium hydroxide solution (7.3N) | 18 g |
| 42° Be strength sodium hydroxide solution (9.5N) | 2.5 g |
| Water q.s. | 100 g |

This cream contains 26.25 ppm of 5-methoxypsoralene.

We claim:

1. A detoxified cosmetic composition suitable for application to the skin in the form of a solution, a lotion, an emulsion, a gel, an aerosol or a solid stick which comprises a natural essence containing a phototoxic dose of at least 10 ppm of furocoumarin, and at least one benzylidenecamphor derivative which filters out Uv-A radiation and reduces the phototoxicity of said furocoumarin, said benzylidenecamphor derivative being selected from the group consisting of:

the 3-p-oxybenzylidenebornan-2-ones of the formula:

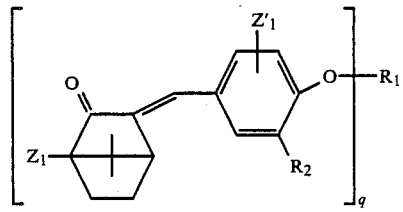

in which:

$Z_1$ and $Z'_1$ respectively denote a hydrogen atom, a radical $SO_3H$ or a salt of this sulphonic acid with an inorganic base, at least one of the two radicals $Z_1$ or $Z'_1$ representing a hydrogen atom;

$R_1$ denotes a hydrogen atom, a linear or branched alkyl radical containing 2 to 18 carbon atoms, an alkienyl radical containing 3 to 18 carbon atoms or a radical

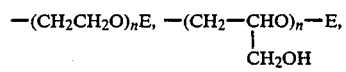

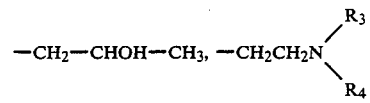

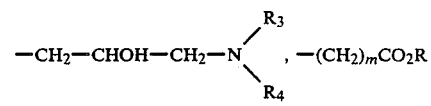

in which R denotes H, an alkyl radical containing 1 to 8 carbon atoms, $-(CH_2)_3-SO_3H$ or a salt of this acid with an organic or inorganic base, or alternatively a divalent radical $-(CH_2)_m$ or $-CH_2-CHOH-CH_2$, m having the values 1 to 10 and n having the values 1 to 6, and $R_3$ and $R_4$ each representing a hydrogen atom or a linear or branched or hydrooxylated alkyl radical, or together forming an aminoaliphatic heterocycle with the nitrogen atom;

$R_2$ denotes a hydrogen atom, an alkoxy radical containing I to 4 carbon atoms or a divalent radical-O-joined to the radical $R_1$ in the case where the latter is also divalent; and c denotes 1 or 2, is being understood that if c has the value 2, $R_1$ is a divalent radical, and that if $R_1$ denotes hydrogen, $R_2$ also denotes hydrogen; moreover, if $R_2$ denotes alkoxy, $R_1$ can also denote methyl;

the benzylidenecamphor derivatives of the formula:

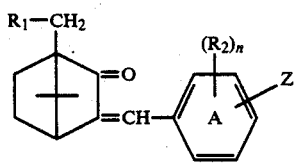

in which:
R₁ denotes a hydrogen atom or a radical —SO₃⊖M⊕, in which M denotes a hydrogen atom, an alkali metal or a group

R₃ denoting a hydrogen atom or a C₁ to C₄ alkyl or hydroxyalkyl radical;
n=0, that is to say R₂ denotes a hydrogen atom; and Z represents a group

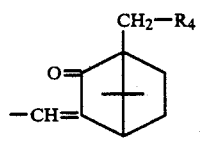

in which R₄ has the same meanings as R₁ and can be equal to R₁ or different from R₁, or alternatively a group

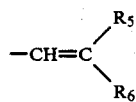

In which R₅ denotes a hydrogen atom, a C₁ to C₄ alkyl radical, an aryl radical unsubstituted or substituted by halogen atoms or by C₁ to C₄ alkyl or alkoxy groups, or a group —CN, —COOR₇ or

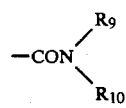

and R₆ denotes a group —COOR₈ or

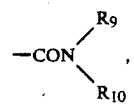

R₇ and R₈, which are identical or different, being alkyl, alkenyl, cycloalkyl or aralkyl radicals containing at most 20 carbon atoms, which are unsubstituted or substituted by hydroxyl, alkoxy, amine or quaternary ammonium groups, and R₉ and R₁₀, which are identical or different, denoting a hydrogen atom or alkyl, alkenyl, cycloalkyl or aralkyl radicals containing at most 20 carbon atoms, which are unsubstituted or substituted by hydroxyl, alkoxy, amine or quaternary ammonium groups, or alternatively if R₅ denotes a hydrogen atom or an alkyl or unsubstituted or substituted aryl radical, R₆ can also represent a radical —COO⊖M⊕, being defined as above, the methylidenecamphor radical, on the one hand, and Z, on the other hand, being attached to the aromatic nucleus A in the para position relative to one another; and
the sulphonates derived from 3-benzylidene-camphor of the formula:

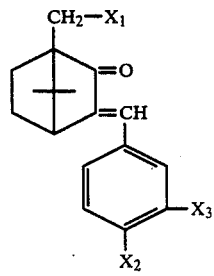

in which
X₁ denotes the radical Y;
X₂ denotes a radical Z; and
X₃ denotes a hydrogen atom,
Y denoting the group

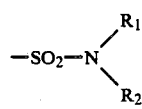

in which
R₁ denotes a hydrogen atom or a C₁ –C₄ alkyl or hydroxyalkyl radical and R₂ denotes a hydrogen atom, a
linear or branched alkyl or alkenyl radical or a cycloalkyl, aryl or aralkyl radical, it being possible for these various C₁–C₂₀ radicals to be substituted by one or more hydroxy, alkoxy or dialkylamino groups, it being impossible for R₁ and R₂ simultaneously to denote a hydrogen atom, and Z denoting one of the following groups:

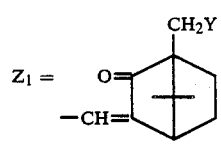

2. Cosmetic composition according to claim 1, wherein said the benzylidene-camphor derivative filtering out UV-A radiation is at least one compound selected from the group consisting of 4'-butoxy-3'-methoxy-3-benzylidenebornanone, 3,3'-terephthalylidenedicampho-10-sulphonic acid, 3,3'-terephthalylidenedicampho-10,10'-disulphonic acid, 4-(ethyl 2'-carboxyethylacrylate)-benzylidenecamphor and also their salts.

3. Cosmetic composition according to claim 1, which further contains at least one compound which filters out UV-B radiation which is compatible with the UV-A filters mentioned in claim 1 or 2 and is selected from the group consisting of:
benzylidenecamphor;
p-methylbenzylidenecamphor;
benzylidenecamphor derivatives containing a quaternary ammonium radical on the benzene nucleus in the par position relative to the bornylidene radical, of the formula:

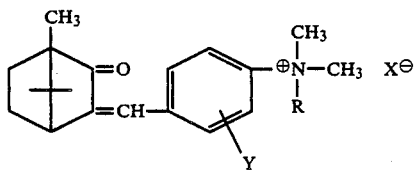

in which:
R represents a hydrogen atom or an alkyl group containing 1 to 12 carbon atoms,
Y represents a halogen, a methyl group or a hydrogen atom, and
$X^\ominus$ a halide, an arylsulphonate, an alkylsulphonate, a camphosulphonate or an alkylsulphate,
benzylidenecamphor derivatives sulphonated on the methyl radical in the 10-position of the camphor or in the 3'-position or 4'-position on the benzene nucleus, having the formulae:

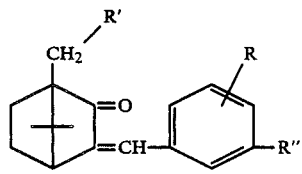

in which R denotes a hydrogen atom, a halogen atom such as $C_1$ or F, or an alkyl radical containing 1 to 4 carbon atoms, and R' and R" each denote a hydrogen atom or a al $-SO_3M$, in which M denotes H, an organic idium group or a metal, at least one of the radicals R' and R" not having the meaning H, and

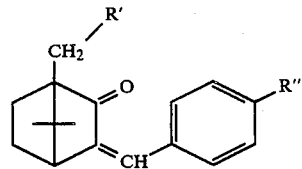

in which R' denotes a hydrogen atom or a radical $-SO_3M$ and R" denotes $SO_3M$, in which M denotes H, an organic ammonium group or a metal;
p-methylbenzylidenecamphor derivatives substituted on the p-methyl group, having the formulae:

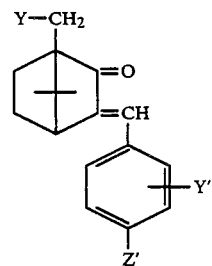

in which Y and Y' denote H or $SO_3H$ and the corresponding salts with organic or inorganic bases, at least one of the radicals Y and Y' having the meaning H; and Z' denotes the group $-CH_2R$, $-CHR'R'$, $-CHO$ or $-COOR"$, in which $R=-OR_4$, $-OCOR_5$, $-SR_6$, $-CN$ or $-COOR"$, $R_4=$w, alkyl, polyoxyethylene or substituted or unsubstituted aryl, $R_5=$alkyl, alkenyl, aryl or an aromatic or non-aromatic heterocycle containing 5 to 6 ring -embers, and $R_6=$H, alkyl, carboxyalkyl, aminoalkyl, hydroxyalkyl, aryl or alanin-3-yl, $R'=-OR'_4$ or $-SR'_6$, in which $R'_4$ and $R'_6$ can respectively have the same meanings as $R_4$ and $R_6$, except for the meaning hydrogen, and $R"=$hydrogen or alkyl, and

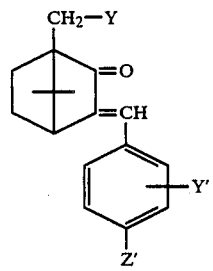

in which Y denotes H or $SO_3H$ and the corresponding salts with organic or inorganic bases;
Y' denotes H; and
Z' denotes the group $-CH_2I$, $-CH_2R$, $-CHR'R'$, $-CHO$ or $-COOR"$, in which $R=OR_4$, $-OCOR_5$, $-SR_6$, $-CN$ or $-COOR"$, $R_4=$H, alkyl, polyoxyethylene, substituted or unsubstituted aryl, methyl or dialkylaminoalkyl, $R_5=$alkyl, alkenyl, aryl or an aromatic or non-aromatic heterocycle containing 5 to 6 ring members, and $R_6=$H, alkyl, carboxyalkyl, aminoalkyl, hydroxyalkyl, aryl or alanin-3-yl, $R'=-OR'_4$ or $-SR'_6$, in which $R'_4$ and $R'_6$ can respectively have the same meanings as $R_4$ and $R_6$, except for the meanings hydrogen, polyoxyethylene, hydroxyalkyl, alanin-3-yl and aryl, and $R"=$hydrogen or alkyl;
the benzylidenecamphor derivatives of the formula:

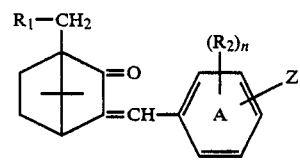

in which:
$R_1$ denotes a hydrogen atom or a radical $-SO_3^\ominus M^\oplus$, in which M denotes a hydrogen atom, an alkali metal or a group $$\overset{\oplus}{N}(R_3)_4,$$

$R_3$ denoting a hydrogen atom or a $C_1$ to $C_4$ alkyl or hydroxyalkyl radical; $R_2$ denotes a linear or branched $C_1$ to $C_4$ alkyl radical or a $C_1$ to $C_4$ alkoxy radical, n being an integer ranging from 0 to 4; if $n \geq 2$, the radicals $R_2$ can be identical or different; and Z represents a group

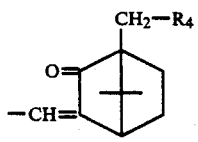

which R$_4$ has the same meanings as R$_1$ and can be equal to R$_1$ or different from R$_1$, or alternatively a group

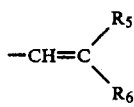

in which R$_5$ denotes a hydrogen atom, a C$_1$ to C$_4$ alkyl radical, an aryl radical unsubstituted or substituted by halogen atoms or by C$_1$ to C$_4$ alkyl or alkoxy groups, or a group —CN, —COOR$_7$ or

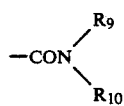

and R$_6$ denotes a group —COOR$_8$ or

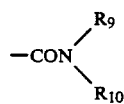

R$_7$ and R$_8$, which are identical or different, being alkyl, alkenyl, cycloalkyl or aralkyl radicals containing at most 20 carbon atoms, which are unsubstituted or substituted by hydroxyl, alkoxy, amine or quaternary ammonium groups, and R$_9$ and R$_{10}$, which are identical or different, denoting a hydrogen atom or alkyl, alkenyl, cycloalkyl or aralkyl radicals containing at most 20 carbon atoms, which are unsubstituted or substituted by hydroxyl, alkoxy, amine or quaternary ammonium groups, or alternatively if R$_5$ denotes a hydrogen atom or an alkyl or unsubstituted or substituted aryl radical, R$_6$ can also represent a radical —COO$^\ominus$M$^\oplus$, M being defined as above, the methylidenecamphor radical, on the one hand, and Z, on the other hand, being attached to the aromatic nucleus A in the meta position relative to one another; they can be attached in the para position if n≠0;

the sulphonamides derived from 3-benzylidenecamphor of the formula:

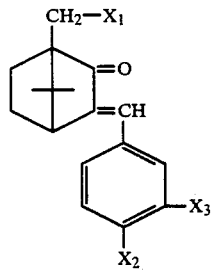

in which X$_1$ denotes a hydrogen atom or the radical Y; X$_2$ denotes a hydrogen or halogen atom, a C$_1$-C$_4$ alkyl or alkoxy radical or a radical Y or Z; and X$_3$ denotes a hydrogen or halogen atom, a C$_1$-C$_4$ alkyl or alkoxy radical or a radical Y or Z, or alternatively X$_2$ and X$_3$ together form an alkylenedioxy group in which the alkylene group contains 1 or 2 carbon atoms, Y denoting the group

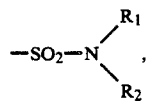

in which R$_1$ denotes a hydrogen atom or a C$_1$-C$_4$ alkyl or hydroxyalkyl radical and R$_2$ denotes a hydrogen atom, a linear or branched alkyl or alkenyl radical or a cycloalkyl, aryl or aralkyl radical, it being possible for these various C$_1$-C$_{20}$ radicals to be substituted by one or more hydroxyl, alkoxy or dialkylamino groups, it being impossible for R$_1$ and R$_2$ simultaneously to denote a hydrogen atom, and Z denoting one of the following groups:

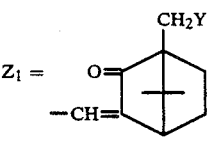

in which Y has the abovementioned meaning, or Z$_2$=

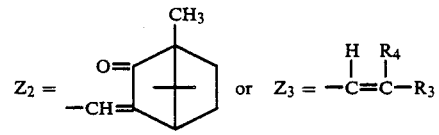

in which R$_3$ denotes a hydrogen atom or a group —CN or —COR$_5$ and R$_4$ denotes a group —COR$_6$, R$_5$ and R$_6$, which are identical or different, being C$_1$-C$_{20}$ alkoxy or alkylamino groups, with the proviso that one of the symbols X$_1$, X$_2$ and X$_3$ is different from the other two and that (a) when X$_1$ denotes a hydrogen atom, X$_2$ and X$_3$ are different from one another and cannot take the meanings Z$_2$ and Z$_3$, one of the two necessarily having the meaning Y or Z$_1$, and (b) when X$_1$ has the meaning Y, X$_2$ and X$_3$ are different from Y and cannot simultaneously take the meaning Z$_1$, Z$_2$ or Z$_3$, and, moreover, if X$_2$= Z$_1$ or Z$_2$, X$_3$ does not denote a hydrogen atom.

4. Cosmetic composition according to claim 3, characterised in that it contains, as compounds filtering out UV-B radiation, at least one compound selected from the group consisting of p-methylbenzylidenecamphor, 4-[(2-oxo-3-bornylidene)-methyl ]-phenyltrimethylammonium methyl-sulphate, N-(2-ethylhexyl)-3-benzylidenecampho-10-sulphonamide, 3-(2-oxo-3-bornylidenemethyl)-benzenesulphonic acid, 2-methyl-5-(2-oxo-3-bornylidenemethyl)-benzenesulphonic acid, 3-benzylidene-2-oxobornane-10-sulphonic acid and also their salts.

5. Cosmetic composition according to claim 1, characterised in that the natural essence is chosen from bergamot oil and lemon oil.

6. The cosmetic composition according to claim 1, characterized in that it contains between about 0.01% and about 2% by weight of benzylidenecamphor derivative relative to the total weight of the composition.

7. Cosmetic composition according to claim 1 which further comprises at least one cosmetic adjuvant selected from the group consisting of thickeners, emollients, wetting agents, surface-active agents, preservatives, anti-foam agents, oils, waxes, dyestuffs and pigments.

8. Cosmetic composition according to claim 1, which is in the form of a cream or a milk comprising fatty alcohols, fatty acid esters or fatty acid triglycerides, fatty acids, lanoline, natural and synthetic oils, and waxes, in the presence of water.

9. Cosmetic composition according to claim 1, which is in the form of an oily-alcoholic lotion comprising at least one lower alcohol selected from the group consisting of ethanol, propylene glycol, and glycerol, and at least one of fatty acid esters and fatty acid triglycerides.

10. Cosmetic composition according to claim 1, which is in the form of an oily-alcoholic gel comprising at least one lower alcohol selected from the group consisting of ethanol, propylene glycol and glycerol, and a thickener, in the presence of oil.

11. Cosmetic composition according to claim 1 which is in the form of a shaving cream or foam comprising soaps.

12. A composition according to claim 11 wherein said soap further comprises fatty acids and softeners.

13. A composition according to claim 11 wherein said soap further comprises foam stabilizers.

14. The cosmetic composition of claim 6 wherein the benzylidenecamphor derivative is present in an amount of between about 0.1% and about 1% by weight relative to the total weight of the composition.

15. A method for detoxifying a cosmetic composition suitable for application to the skin comprising a natural essence containing a phototoxic dose of at least 10 ppm of a furocoumarin comprising:

adding to said cosmetic composition at least one benzylidenecamphor capable of filtering out UV-A radiation in an amount effective to reduce the phototoxicity of said furocoumarin, said benzylidenecamphor derivative being selected from the group consisting of:

the 3-p-oxybenzylidenebornan-2-ones of the formula:

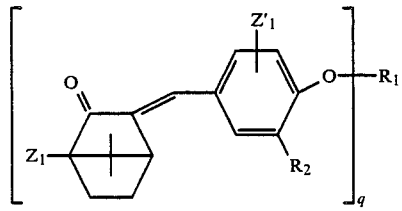

in which:

$Z_1$ and $Z'_1$ respectively denote a hydrogen atom, a radical $SO_3H$ or a salt of this sulphonic acid with an inorganic or organic, base, at least one of the two radicals $Z_1$ or $Z'_1$ representing a hydrogen atom;

$R_1$ denotes a hydrogen atom, a linear or branched alkyl radical containing 2 to 15 carbon atoms, an alkenyl radical containing 3 to 8 carbon atoms or a radical

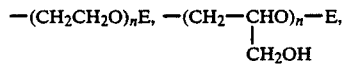

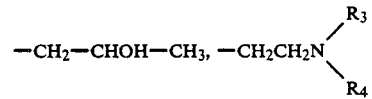

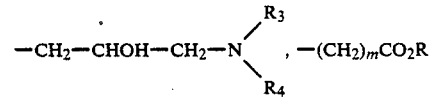

in which R denotes H, an alkyl radical containing 1 to 8 carbon atoms, $-(CH_2)_3-SO_3H$ or a salt of this acid with an organic or inorganic base, or alternatively a divalent radical $-(CH_2)_m$ or $-CH_2-CHOH-CH_2$, m having the values 1 to 10 and n having the values 1 to 6, and $R_3$ and $R_4$ each representing a hydrogen atom or a linear or branched or hydroxylated alkyl radical, or together forming an aminoaliphatic heterocycle with the nitrogen atom;

$R_2$ denotes a hydrogen atom, an alkoxy radical containing 1 to 4 carbon atoms or a divalent radical-0-joined to the radical $R_1$ in the case where the letter is also divalent; and c denotes 1 or 2, it being understood that if c has the value 2, $R_1$ is a divalent radical, and that if $R_1$ denotes hydrogen, $R_2$ also denotes hydrogen; moreover, if $R_2$ denotes alkoxy, $R_1$ can also denote methyl;

the benzylidenecamphor derivatives of the formula:

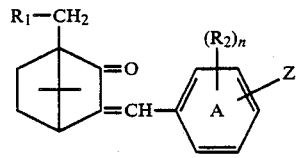

in which:

$R_1$ denotes a hydrogen atom or a radical $-SO_3^{\ominus}M^{\oplus}$ in which M denotes a hydrogen atom, an alkali metal or a group

$R_3$ denoting a hydrogen atom or a $C_1$ to $C_4$ alkyl or hydroxyalkyl radical;

n=0, that is to say $R_2$ denotes a hydrogen atom; and Z represents a group

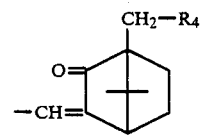

in which $R_4$ has the same meanings as $R_1$ and can be equal to $R_1$ or different from $R_1$, or alternatively a group

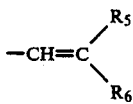

in which R₅ denotes a hydrogen atom, a C₁ to C₄ alkyl radical, an aryl radical unsubstituted or substituted by halogen atoms or by C₁ to C₄ alkyl or alkoxy groups, or a group —CN, —COOR₇ or

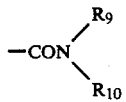

and R₆ denotes a group —COOR₈ or

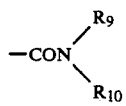

R₇ and R₈, which are identical or different, being alkyl, alkenyl, cycloalkyl or aralkyl radicals containing at most 20 carbon atoms, which are unsubstituted or substituted by hydroxyl, alkoxy, amino or quaternary ammonium groups, and R₉ and R₁₀, which are identical or different, denoting a hydrogen atom or alkyl, alkenyl, cycloalkyl or aralkyl radicals containing at most 20 carbon atoms, which are unsubstituted or substituted by hydroxyl, alkoxy, amine or quaternary ammonium groups, or alternatively if R₅ denotes a hydrogen atom or an alkyl or unsubstituted or substituted aryl radical, R₆ can also represent a radical —COO⁶³ M⊕, M being defined as above, the methylidenecamphor radical, on the one hand, and Z, on the other hand, being attached to the aromatic nucleus A in the para position relative to one another; and the sulphonamides derived from 3-benzylidenecamphor of the formula:

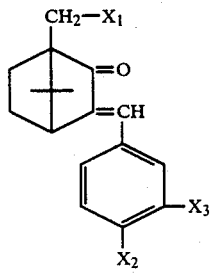

in which:
X₁ denotes the radical Y;
X₂ denotes a radical Z; and
X₃ denotes a hydrogen atom,
Y denoting the group

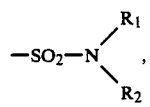

in which R₁ denotes a hydrogen atom or a C₁–C₄ alkyl or
hydroxyalkyl radical and R₂ denotes a hydrogen atom, a linear or branched alkyl or alkenyl radical or a cycloalkyl, aryl or aralkyl radical, it being possible for these various C₁–C₂₀ radicals to be substituted by one or more hydroxyl, alkoxy or dialkylamino groups, it being impossible for R₁ and R₂ simultaneously to denote a hydrogen atom, and Z denoting one of the following groups:

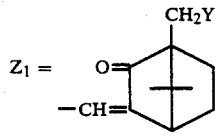

in which Y has the abovementioned meaning, or

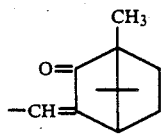

16. The method of claim 15 wherein the benzylidenecamphor derivative is present in an amount of between about 0.01% and about 2% by weight relative to the total weight of the composition.

17. The method of claim 15 wherein the benzylidenecamphor derivative is selected from the group consisting of: 4'-butoxy-3'-methoxy-3-benzylidenebornanone, 3,3'-terephthalylidenedicampho-10-sulphonic acid, 3,3'-terephthalylidenedicampho-10,10'-disulphonic acid, 4 (ethyl 2-carboxyethylacrylate)-benzylidenecamphor and salts thereof.

18. The method of claim 15 comprising further adding to said cosmetic composition at least one compound capable of filtering out UV-B radiation being compatible with the benzylidenecamphor derivatives capable of filtering UV-A radiation; said UV-B filtering compound being selected from the group consisting of:
benzylidenecamphor;
p-methylbenzylidenecamphor;
benzylidenecamphor derivatives containing a quaternary ammonium radical on the benzene nucleus in the para position relative to the benzylidene radical, of the formula:

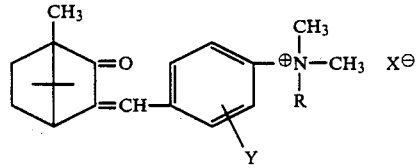

in which:
R represents a hydrogen atom or an alkyl group containing 1 to 12 carbon atoms,
Y represents a halogen, a methyl group or a hydrogen atom, and
X⊖ represents a halide, an arylsulphonate, an alkylsulphonate, a camphosulphonate or an alkylsulphate;
benzylidenecamphor derivatives sulphonated on the methyl radical in the 10-position at the camphor or in the 3'-position or 4'-position on the benzene nucleus, having the formulae:

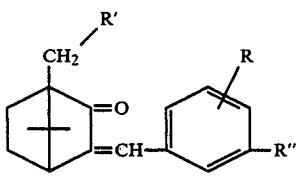

in which R denotes a hydrogen atom, a halogen atom such as Cl or F, or an alkyl radical containing 1 to 4 carbon atoms, and R' and R" each denote a hydrogen atom or a radical —$SO_3M$, in which M denotes H, an organic ammonium, group or a metal, at least one of the radicals R' and R" not having the meaning H, and

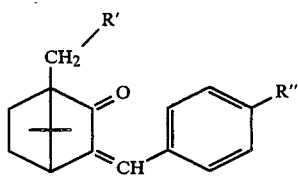

in which R', denotes a hydrogen atom or a radical —$SO_3M$ and R" denotes $SO_3M$, in which M denotes H, an organic ammonium group or a metal;

p-methylbenzylidenecamphor derivatives substituted on the p-methyl group, having the formulae:

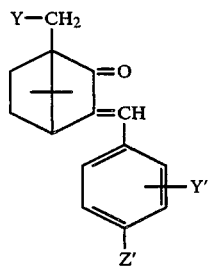

in which Y and Y' denote H or $SO_3H$ and the corresponding salts with organic or inorganic bases, at least one of the radicals Y and Y' having the meaning H; and Z' denotes the group —$CH_2R$, —CHR'R', —CHO or —COOR", in which R=—$OR_4$, —$OCOR_5$, —$SR_6$, —CN or —COOR", $R_4$=H, alkyl, polyoxyethylene or substituted or unsubstituted aryl, $R_5$=alkyl alkenyl, aryl or an aromatic or an non-aromatic heterocycle containing 5 to 6 ring members, and $R_6$=H, alkyl, carboxyalkyl, aminoalkyl, hydroxyalkyl, aryl or alanin3-yl, R'=—$OR'_4$ or —$SR'_6$, in which $R'_4$ and $R'_6$ can respectively have the same meanings as $R_4$ and $R_6$, except for the meaning hydrogen, and R"=hydrogen or alkyl, and

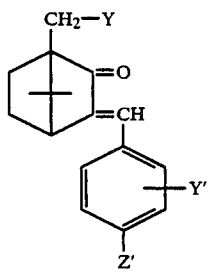

in which Y denotes H or $SO_3H$ and the corresponding salts with organic or inorganic bases;
Y' denotes H; and
Z' denotes the group —$CH_2I$, —$CH_2R$, —CHR'R', —CHO or —COOR", in which R=$OR_4$, —$OCOR_5$, —$SR_6$, —CN or —COOR", $R_4$ =H, alkyl, polyoxyethylene, substituted or unsubstituted aryl, menthyl or dialkylaminoalkyl, $R_5$=alkyl, alkenyl, aryl or an aromatic or non-aromatic heterocycle containing 5 to 6 ring members, and $R_6$ =H, alkyl, carboxyalkyl, aminoalkyl,, hydroxyalkyl, aryl or alanin-3-yl, R'=—$OR'_4$ or —$SR'_6$, in which $R'_4$ and $R'_6$ can respectively have the same meanings as $R_4$ and $R_6$, except for the meanings hydrogen, polyoxyethylene, hydroxyalkyl, alanin-3-yl and aryl, and R"=hydrogen or alkyl;
the benzylidenecamphor derivative of the formula:

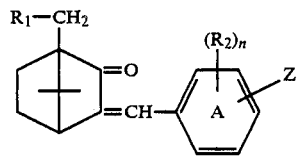

in which:
$R_1$ denotes a hydrogen atom, or a radical —$SO_3^{\ominus} M^{\oplus}$, in which M denotes a hydrogen atom, an alkali metal or a group

$N(R_3)_4$, $R_3$ denoting a hydrogen atom or a $C_1$ to $C_4$ alkyl hydroxyalkyl radical;
$R_2$ denotes a linear or branched $C_1$ to $C_4$ alkyl radical or a $C_1$ to $C_4$ alkoxy radical, n being an integer ranging from 0 to 4; if n≧2, the radicals $R_2$ can be identical or different; and
Z represents a group

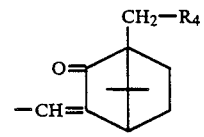

in which $R_4$ has the same meanings as $R_1$ and can be equal to $R_1$ or different from $R_1$, or alternatively a group

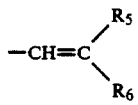

in which R₅ denotes a hydrogen atom, a C₁ to C₄ alkyl radical, an aryl radical unsubstituted or substituted by halogen atoms or by C₁ to C₄ alkyl or alkoxy groups, or a group —CN, —COOR₇ or

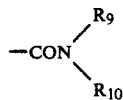

and R₆ denotes a group —COOR₈ or

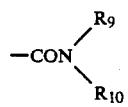

R₇ and R₈, which are identical or different, being alkyl, alkenyl, cycloalkyl or aralkyl radicals containing at most 20 carbon atoms, which are unsubstituted or substituted by hydroxyl, alkoxy, amine or quaternary ammonium groups, and R₉ and R₁₀, which are identical or different, denoting a hydrogen atom or alkyl, alkenyl, cycloalkyl or aralkyl radicals containing at most 20 carbon atoms, which are unsubstituted or substituted by hydroxyl, alkoxy, amine or quaternary ammonium groups, or alternatively if R₅ denotes a hydrogen atom or an alkyl or unsubstituted or substituted aryl radical, R₆ can also represent a radical —COO⊖M⊕, M being defined as above, the methylidenecamphor radical, on the one hand, and Z, on the other hand, being attached to the aromatic nucleus A in the meta position relative to one another; they can be attached in the para position if n≠0; and the sulphonamides derived from 3-benzylidene-camphor of the formula:

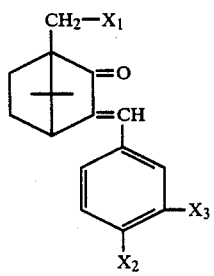

in which X denotes a hydrogen atom or the radical Y;
X₂ denotes a hydrogen or halogen atom, a C₁–C₄ alkyl or alkoxy radical or a radical 1 or 2; and X₃ denotes a hydrogen or halogen atom, a C₁–C₄ alkyl or alkoxy radical or a radical Y or Z, or alternatively X₂ and X₃ together form an alkylenedioxy group in which the alkylene group contains 1 or 2 carbon atoms, Y denoting the group

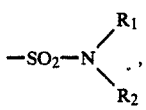

in which R₁ denotes a hydrogen atom or a C₁–C₄ alkyl or hydroxyalkyl radical and R₂ denotes a hydrogen atom, a linear or branched alkyl or alkenyl radical or a cycloalkyl, aryl or aralkyl radical, it being possible for these various C₁–C₂₀ radicals to be substituted by one or more hydroxyl, alkoxy or dialkylamino groups, it being impossible for R₁ and R₂ simultaneously to denote a hydrogen atom, and Z denoting one of the following groups:

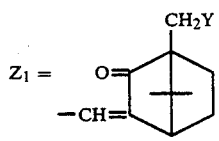

in which Y has the abovementioned meaning, or

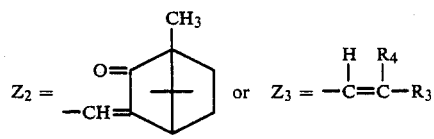

in which R₃ denotes a hydrogen atom or a group —CN or —COR₅ and R₄ denotes a group —COR₆, R₅ and R₆, which are identical or different, being C₁–C₂₀ alkoxy or alkylamino groups, with the proviso that one of the symbols X₁, X₂ and X₃ is different from the other two and that
(a) when X₁ denotes a hydrogen atom, X₂ and X₃ are different from one another and cannot take the meanings Z₂ and Z₃, one of the two necessarily having the meaning Y or Z₁, and
(b) when X₁ has the meaning Y, X₂ and X₃ are different from Y and cannot simultaneously take the meaning Z₁, Z₂ or Z₃, and, moreover, if X₂ =Z₁ or Z₂, X₃ does not denote a hydrogen atom.

19. The method of claim 18 wherein the compound capable of filtering out UV-B radiation is selected from the group consisting of:
p-methylbenzylidenecamphor, 4-[(2-oxo-3-bornylidene)-methyl]-phenyltrimethylammonium methyl sulphate, N-(2-ethylhexyl)-3-benzylidenecampho-10-sulphonamide, 3-(2-oxo-3-bornylidenemethyl)-benzenesulphonic acid, 2-methyl-5-(2-oxo-3-bornylidenemethyl)-benzenesulphonic acid, 3-benzylidene-2-oxobornane-10-sulphonic acid and salts thereof.

20. The method of claim 15 wherein the benzylidenecamphor derivative is present in an amount of between about 0.1% and about 1% by weight relative to the total weight of the composition.

* * * * *